US00PP33843P2

(12) United States Plant Patent
Trees

(10) Patent No.: US PP33,843 P2
(45) Date of Patent: Jan. 11, 2022

(54) ***BUDDLEJA* PLANT NAMED 'BALCHRYINK'**

(50) Latin Name: ***Buddleja* hybrid**
Varietal Denomination: Balchryink

(71) Applicant: Ball Horticultural Company, West Chicago, IL (US)

(72) Inventor: Scott C. Trees, Arroyo Grande, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 17/400,277

(22) Filed: Aug. 12, 2021

(51) Int. Cl.
*A01H 5/02* (2018.01)
*A01H 6/00* (2018.01)

(52) U.S. Cl.
USPC ..... Plt./242

(58) Field of Classification Search
USPC ..... Plt./242
CPC ... A01H 5/02; A01H 5/00; A01H 6/00; A01H 6/14; A01H 6/30
See application file for complete search history.

*Primary Examiner* — June Hwu
(74) *Attorney, Agent, or Firm* — Audrey Charles

(57) ABSTRACT

A new and distinct cultivar of *Buddleja* plant named 'Balchryink', characterized by its light purplish-pink colored flowers, dark green-colored foliage, low growth vigor, and compact-mounded growth habit, is disclosed.

2 Drawing Sheets

Latin name of genus and species of plant claimed: *Buddleja* hybrid.

Variety denomination: 'Balchryink'.

BACKGROUND OF THE INVENTION

The present invention relates to a new and distinct cultivar of *Buddleja* plant botanically known as *Buddleja hybrid* and hereinafter referred to by the cultivar name 'Balchryink'.

The new cultivar originated in a controlled breeding program in Guadalupe, Calif. during the summer of 2018. The objective of the breeding program was the development of *Buddleja* cultivars having numerous inflorescences with distinctive coloration, repeat blooming, and a highly branched, compact-mounded growth habit.

The new *Buddleja* cultivar is the result of open-pollination. The female (seed) parent of the new cultivar is Buzz Hot Raspberry 'Tobud1202', U.S. Plant Patent applied for, characterized by its deep, red-purple colored flowers having an orange center, medium green colored foliage, and moderately vigorous, compact-mounded growth habit. The male (pollen) parent of the new cultivar is unknown. The new cultivar was selected as a single flowering plant within the progeny of the above stated open-pollination during April 2019 in a controlled environment in Guadalupe, Calif.

Asexual reproduction of the new cultivar by terminal stem cuttings since April 2019 in Guadalupe, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balchryink' as a new and distinct cultivar of *Buddleja* plant:

1. Light purplish-pink colored flowers;
2. Dark green-colored foliage;

3. Low growth vigor; and
4. Compact-mounded growth habit.

Plants of the new cultivar differ from plants of the female parent in having light purplish-pink colored flowers and reduced growth vigor.

Of the many commercially available *Buddleja* cultivars, the most similar in comparison to the new cultivar is Buzz Purple 'Tobudpipur', U.S. Plant Pat. No. 22,064. However, in comparison, plants of the new cultivar differ from plants of 'Tobudpipur' in at least the following characteristics:

1. Plants of the new cultivar have smaller diameter corollas than plants of 'Tobudpipur'; and
2. Plants of the new cultivar have lighter, purplish-pink colored flowers than plants of 'Tobudpipur'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balchryink'. The plants were approximately five-months old. The plants were grown for approximately 9 weeks in three-quart containers in an outdoor nursery in West Chicago, Ill. Plants were given two pinches prior to transplant and one pinch one week after transplant.

DETAILED BOTANICAL DESCRIPTION

Figure 1:
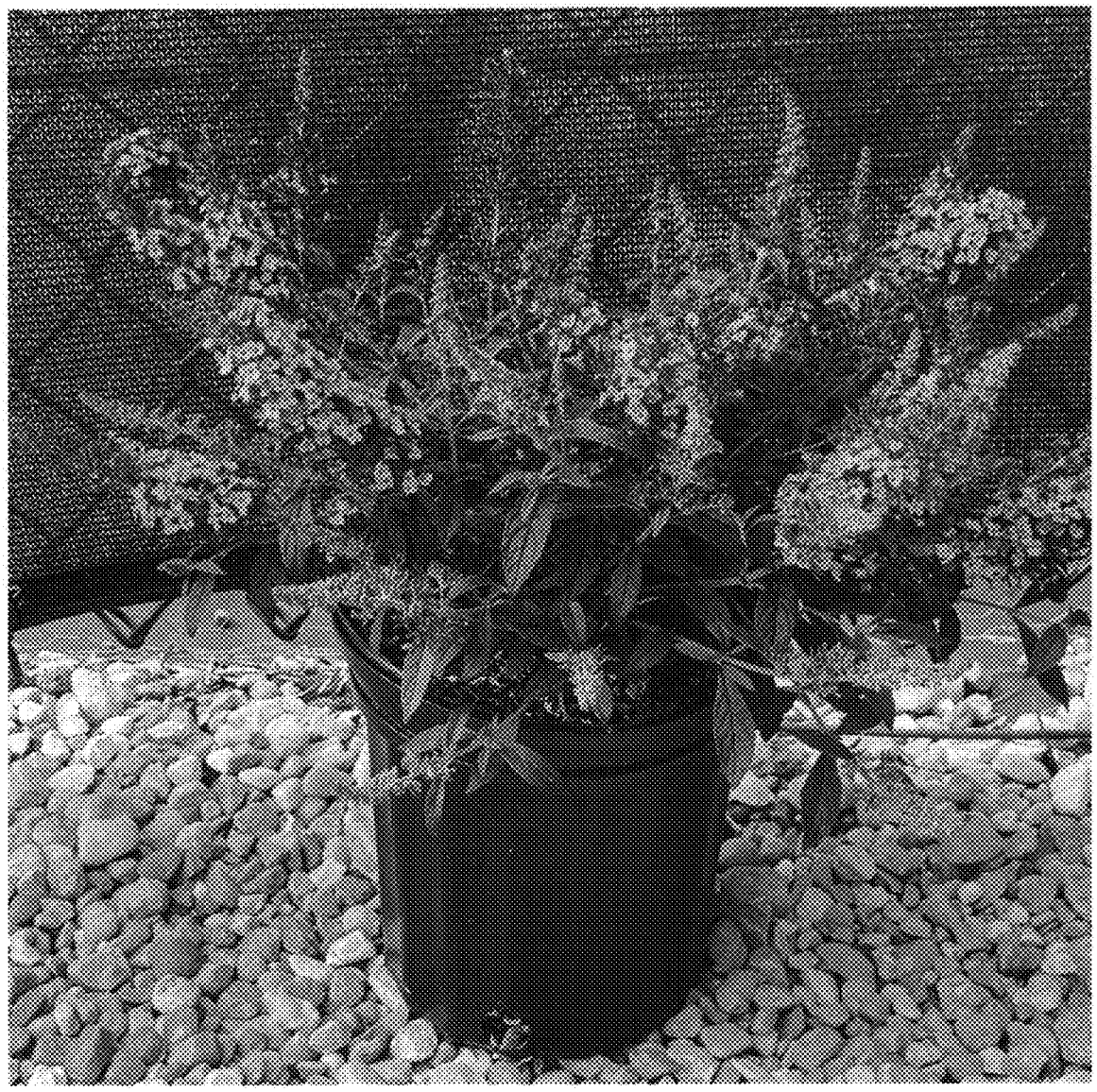
FIG. 1 illustrates a side view of the overall growth and flowering habit of 'Balchryink'.
Figure 2:
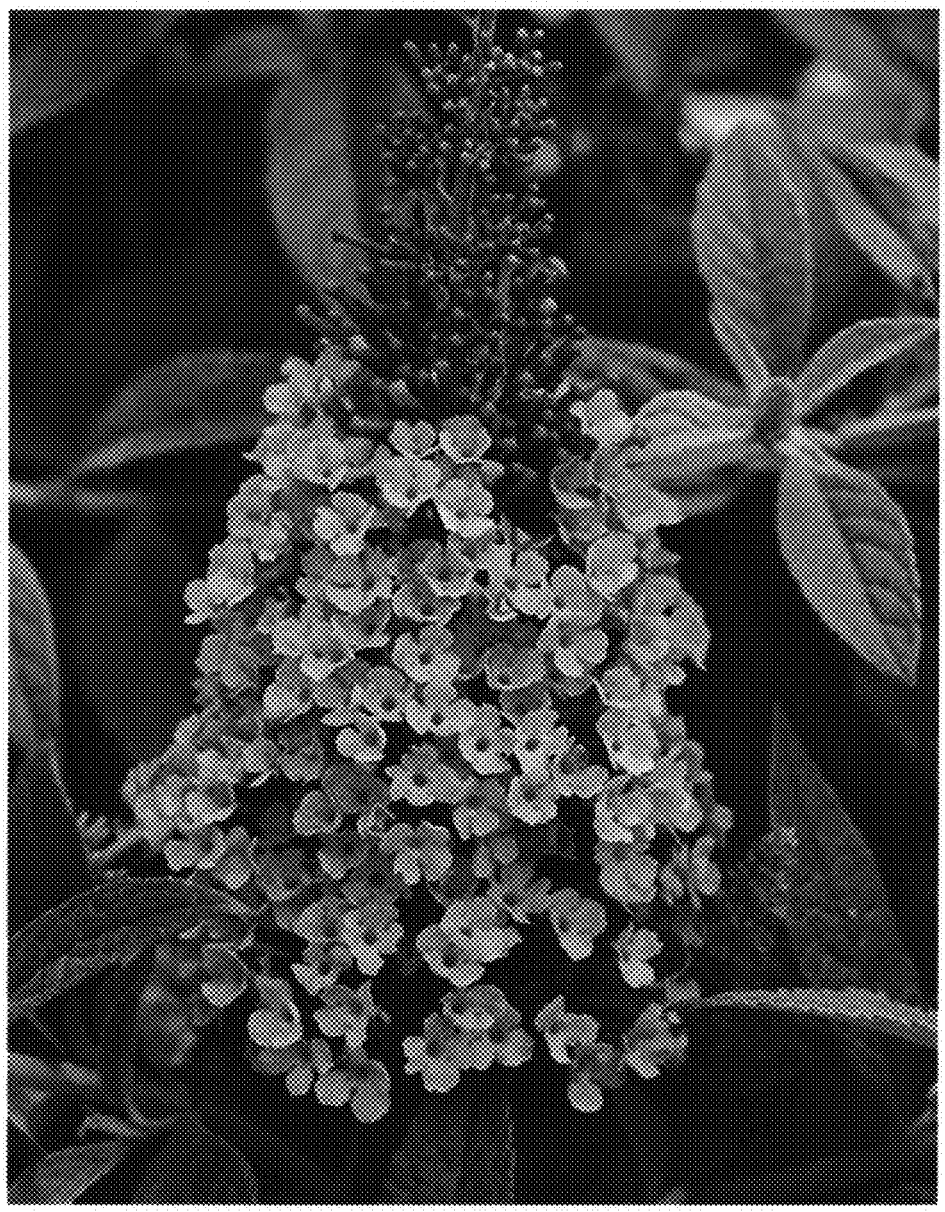
FIG. 2 illustrates a close-up view of an individual inflorescence of 'Balchryink'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in July 2021 under natural light conditions in Naperville, Ill.

The following descriptions and measurements describe approximately five-month-old plants produced from cuttings from stock plants and grown under conditions comparable to those used in commercial practice. The plants were grown in three-quart containers for approximately 9 weeks in an outdoor nursery in West Chicago, Ill. Plants were given two pinches prior to transplant and one pinch one week after transplant. Prior to transplant plants were grown in liners in a poly-covered greenhouse in West Chicago, Ill. Greenhouse temperatures ranged from an average high of 79.5° F. (26.4° C.) to an average low of 68.5° F. (20.3° C.), and supplemental lighting was provided daily for five hours during short days. Measurements and numerical values represent averages of typical plants.

Botanical classification: *Buddleja hybrid* 'Balchryink'.

Parentage:

*Female parent*.—Buzz Hot Raspberry 'Tobud1202', U.S. Plant Patent applied for.

*Male parent*.—Unknown.

Propagation:

*Type cutting*.—Terminal stem.

*Time to initiate roots*.—Approximately 14 to 20 days.

*Time to produce a rooted cutting*.—Approximately 6 to 7 weeks.

*Root description*.—Fine, fibrous.

*Rooting habit*.—Freely branching, moderately dense.

Plant description:

*Commercial crop time*.—Approximately 8 to 10 weeks from a rooted cutting to finish in a one-gallon container.

*Growth habit and general appearance*.—Low growth vigor, compact-mounded.

*Hardiness*.—USDA Zone 5a (−20° F. to −15° F./−28.9 ° C. to −26° C.).

*Size*.—Height from soil level to top of plant plane: Approximately 20.0 cm. Width: Approximately 45.0 cm.

*Branching habit*.—Freely branching. Pinching enhances lateral branching. Quantity of branches per plant: Approximately 7 main branches with 4 to 6 laterals on each main branch.

*Lateral branch*.—Shape: Square. Strength: Strong. Length to base of inflorescence: Approximately 8.0 cm. Diameter: Approximately 2.0 mm to 3.0 mm. Length of central internode: Approximately 2.2 cm. Texture of young and mature branches: Densely pubescent with tomentum. Color of young stems: 146D with pubescence of NN155B. Color of mature stems: 146B becoming woody N199A with age, pubescence of NN155B.

Foliage description:

*General description*.—Quantity of leaves per branch: Approximately 8. Fragrance: None detected. Form: Simple. Arrangement: Opposite, decussate.

*Leaves*.—Aspect: Primarily perpendicular to stem. Shape: Elliptic. Margin: Serrulate. Apex: Acute. Base: Attenuate. Venation pattern: Pinnate, reticulate. Length of mature leaf: Approximately 4.0 cm. Width of mature leaf: Approximately 1.4 cm. Texture of upper surface: Sparsely pubescent with glands. Texture of lower surface: Densely pubescent with tomentum. Color of upper surface of young foliage: NN137B with indistinguishable venation. Color of lower surface of young and mature foliage: 191C with venation of 147C. Color of upper surface of mature foliage: NN137A with indistinguishable venation.

*Petiole*.—Length: Approximately 2.0 mm. Diameter: Approximately 2.0 mm. Texture: Densely pubescent with tomentum. Color: 147C.

Flowering description:

*Flowering habit*.—'Balchryink' is freely flowering under outdoor growing conditions blooming from late spring through mid-fall.

*Lastingness of individual flower*.—Approximately 5 to 7 days.

Inflorescence description:

*General description*.—Type: Terminal panicles, each panicle having about 2 to 4 branches. Flowers persistent, facing upward and outward. Quantity of open inflorescences per plant: Approximately 19. Fragrance: Slightly sweet. Depth or height of inflorescence: Approximately 11.0 cm. Width: Approximately 4.0 cm. Quantity of flowers per inflorescence: Approximately 100, opening from base to apex.

*Rachis*.—Strength: Strong. Length: Approximately 10.5 cm. Diameter: Approximately 1.0 mm to 2.0 mm. Texture: Densely pubescent with tomentum. Color: 146D with pubescence of NN155B.

Flower description:

*Type*.—Single, salverform.

*Bud just before opening*.—Shape: Oblong. Length: Approximately 5.0 mm. Diameter: Approximately 1.0 mm. Texture: Sparsely pubescent. Color of petals: N82A.

*Corolla*.—Shape: Rotate, 4 petals arranged in a single whorl. Depth: Approximately 1.1 cm. Width: Approximately 6.0 mm.

*Petals*.—Shape: Rotund. Margin: Erosulate. Apex: Rounded. Length from throat: Approximately 2.5 mm. Width: Approximately 3.0 mm. Texture of upper and lower surfaces: Glabrous. Color of upper surface when first open: N82C with 13B at petal base. Color of lower surface when first and fully open: N82C to N82D. Color of upper surface when fully open: Closest to but more red than N82D with 13B at petal base.

*Corolla tube*.—Length: Approximately 9.0 mm. Width: Approximately 1.0 mm. Diameter of throat opening: Approximately 1.0 mm. Texture of inner and outer surfaces: Sparsely pubescent. Color of inner surface: 34B with 34A at throat opening. Color of outer surface: N77B.

*Calyx*.—Shape: Tubular. Length: Approximately 3.0 mm. Diameter: Approximately 1.0 mm.

*Sepals*.—Quantity per flower: 4, fused at base. Apex: Acute. Margin of free portion: Entire. Length: Approximately 3.0 mm. Width: Less than 1.0 mm. Texture of inner surface: Glabrous. Texture of outer surface: Densely pubescent with tomentum. Color of inner surface: 137A. Color of outer surface: 137B with N186A on tips and pubescence of NN155B.

*Pedicels*.—Strength: Strong, flexible. Length: Approximately 1.0 mm. Diameter: Approximately 1.0 mm. Texture: Densely pubescent with tomentum. Color: 137B with pubescence of NN155B.

*Reproductive organs*.—Androecium: Stamen quantity: 4 per flower, filaments adnate to corolla. Anther shape: Bilobed, divergent. Anther length: Approximately 1.0 mm. Anther color: NN155A. Pollen amount: None observed. Gynoecium: Pistil quantity: 1 per flower. Pistil length: Approximately 4.0 mm. Stigma shape: Cleft, two-parted. Stigma length: Less than 1.0 mm. Stigma color: Closest to 144A. Style length: Approximately 2.0 mm. Style color: Closest to 145D, opaque. Ovary length: Approximately 2.0 mm. Ovary color: Closest to 144B.

Seed and fruit production: Neither seed nor fruit production has been observed.

Disease and pest resistance: Resistance to pathogens and pests common to *Buddleja* has not been observed.

What is claimed is:

1. A new and distinct cultivar of *Buddleja* plant named 'Balchryink', substantially as herein illustrated and described.

* * * * *